United States Patent
Mormul et al.

(10) Patent No.: US 12,398,091 B2
(45) Date of Patent: Aug. 26, 2025

(54) PROCESS FOR THE PURIFICATION OF A MIXTURE COMPRISING N-ALKYL-HYDROXYLAMMONIUM SALTS

(71) Applicant: BASF SE, Ludwigshafen am Rhein (DE)

(72) Inventors: Jaroslaw Michael Mormul, Ludwigshafen am Rhein (DE); Dieter Kolassa, Ludwigshafen am Rhein (DE); Dominic Riedel, Ludwigshafen am Rhein (DE); Joaquim Henrique Teles, Ludwigshafen am Rhein (DE); Ansgar Gereon Altenhoff, Ludwigshafen am Rhein (DE); Richard Dehn, Ludwigshafen am Rhein (DE); Peter Oechsle, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 730 days.

(21) Appl. No.: 17/781,405

(22) PCT Filed: Nov. 23, 2020

(86) PCT No.: PCT/EP2020/083002
§ 371 (c)(1),
(2) Date: Jun. 1, 2022

(87) PCT Pub. No.: WO2021/110445
PCT Pub. Date: Jun. 10, 2021

(65) Prior Publication Data
US 2023/0017999 A1    Jan. 19, 2023

(30) Foreign Application Priority Data

Dec. 2, 2019    (EP) .................................... 19212783

(51) Int. Cl.
*C07C 209/84*    (2006.01)

(52) U.S. Cl.
CPC .................................. *C07C 209/84* (2013.01)

(58) Field of Classification Search
None
See application file for complete search history.

(56) References Cited

U.S. PATENT DOCUMENTS

| 5,731,462 A | 3/1998 | Calais et al. |
| 2004/0149563 A1 | 8/2004 | Wostbrock et al. |

FOREIGN PATENT DOCUMENTS

WO    2007/063327 A1    6/2007

OTHER PUBLICATIONS

International Search Report and Written Opinion received for PCT Patent Application No. PCT/EP2020/083002, mailed on Feb. 17, 2021, 8 pages.

*Primary Examiner* — Renee Claytor
*Assistant Examiner* — Jennifer C Sawyer
(74) *Attorney, Agent, or Firm* — Faegre Drinker Biddle & Reath LLP

(57) ABSTRACT

The present invention relates to a process for purification of a mixture comprising water, N-alkyl-hydroxylammonium salts and some byproducts wherein from the mixture water and byproducts are distilled off until the purity of N-alkyl-hydroxylammonium salts in the residue is 95% or higher and additionally keeping the water content during and after the distillation≥40 wt.-% according to the residue.

13 Claims, No Drawings

PROCESS FOR THE PURIFICATION OF A MIXTURE COMPRISING N-ALKYL-HYDROXYLAMMONIUM SALTS

CROSS-REFERENCE TO RELATED APPLICATIONS

This application is a national stage application (under 35 U.S.C. § 371) of PCT/EP2020/083002, filed Nov. 23, 2020, which claims benefit of European Application No. 19212783.5, filed Dec. 2, 2019, both of which are incorporated herein by reference in their entirety.

The present invention relates to a process for purification of a mixture comprising water, N-alkyl-hydroxylammonium salts and some byproducts wherein from the mixture water and byproducts are distilled off until the purity of N-alkyl-hydroxylammonium salts in the residue is 95% or higher and additionally keeping the water content during and after the distillation≥40 wt.-% according to the residue. This inventive process results to an aqueous mixture comprising N-alkyl-hydroxylammonium salts with a purity of 95% or more and that is easy to handle without any instruction of safety.

N-Alkyl-hydroxylamines or their salts are versatile building blocks for e.g. pharmaceutical compounds.

One route starts from readily available dialkylamines which are oxidized with hydrogen peroxide to yield the corresponding nitrone. The nitrone is hydrolyzed under acidic conditions to the corresponding N-alkyl-hydroxylammonium salt and different kind of byproducts. This synthesis was already published in U.S. Pat. No. 5,731,462 A. However, the main disadvantage of this route is the purification of the product mixture which contains byproducts from both the oxidation and the hydrolytic cleavage. So far, only the isolation of pure product was reported as a way for purification of the product in laboratory scale. However, hydroxylamine derivatives typically feature very high decomposition energies of more than 900 J/g together with low onset temperatures around 100° C. This means that often such hydroxylamines are potentially explosive and not very stable under normal handling conditions. Therefore, the isolation of these hydroxylamines and their use as starting product in further commercial processes is not a viable way regarding current process safety concepts and need expensive extra efforts to handle them.

Therefore, it is the object of the present invention to provide a process which allows the removal of byproducts and additionally to handle the N-alkyl-hydroxylammonium salts in a condition where no danger of explosion exists so that the handling is optimized for commercial processes.

Unexpectedly, it was found that this can be accomplished with a process for the purification of a mixture comprising three compounds:
a) water,
b) 1 to 60 wt.-% of N-alkyl-hydroxylammonium salt of formula I

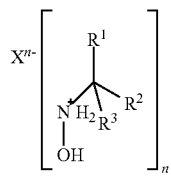

with $R^1$, $R^2$, $R^3$ each independently are selected from the group of H, methyl, ethyl, n-propyl, isopropyl, n-butyl, 2-butyl and tert-butyl,
with X is selected from Cl, $SO_4$, $PO_4$, $CH_3COO$, $(COO)_2$,
with n dependent of the valence of X in water is a natural number selected from the group of 1, 2 and 3 and
c) byproducts
wherein the process comprises the following steps:
I) putting the mixture into a purification apparatus,
II) bringing the mixture in contact with steam
III) removing a composition comprising water vapor and compound c) by distillation until the purity of compound b) in the residue is 95% or greater wherein the amount of water in the residue remains during and after the distillation≥40 wt.-%.

Advantageous is the process of the invention wherein the purification apparatus is a packed column as it is used for a continuous countercurrent flow stripping process.

Advantageous is the process of the invention wherein the purification apparatus is a distillation apparatus.

Advantageous is the process of the invention wherein the purification apparatus is a steam distillation apparatus.

Advantageous is the process of the invention wherein water is added either before step II) and/or during and/or after distillation of step III) of the inventive process.

Advantageous is the process of the invention wherein the water that is added during the distillation of step III) in a steam distillation apparatus or in the packed column as it is used for continuous reverse flow stripping process is added as steam.

Advantageous is the process of the invention wherein water that is added during the distillation of step III) in a distillation apparatus is added according to the following steps:
i) stopping the distillation,
ii) adding the water in liquid form to the residue and
iii) starting the distillation again.

Advantageous is the process of the invention wherein the distillation temperature during step III) is in the range of 10 to 100° C. and the pressure is in the range of 1 to 1000 mbar.

Advantageous is the process of the invention wherein the composition distilled off in step III) comprises more than 50 wt.-% of water.

Advantageous is the process of the invention wherein X is Cl and n is 1.

Advantageous is the process of the invention wherein $R^1$ is ≠$R^2$ and $R^3$ is H.

Advantageous is the process of the invention wherein $R^1$ is methyl, $R^2$ and $R^3$ are H, X is Cl and n is 1.

Advantageous is the process of the invention wherein $R^1$, $R^2$ and $R^3$ is H.

The inventive process for purification starts from a mixture comprising water as compound a), N-alkyl hydroxylammonium salt of formula I as compound b) and byproducts as compound c).

This mixture is obtainable by reacting a dialkylamine with an aqueous hydrogen peroxide solution and hydrolyzing the resulting nitrone under acidic conditions to the corresponding N-alkyl-hydroxylammonium salt as it is disclosed in U.S. Pat. No. 5,731,462 A before removing the water.

The amount of water as compound a) in the mixture is in the range from 40 to 95 wt.-%. Preferred is the amount of water in the range from 40 to 75 wt. %.

The compound b) is an N-alkyl-hydroxylammonium salt of formula I

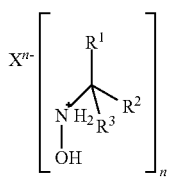

with $R^1$, $R^2$, $R^3$ each independently are selected from the group of H, methyl, ethyl, n-propyl, isopropyl, n-butyl, 2-butyl and tert-butyl. $R^1$, $R^2$, $R^3$ are preferred H and/or methyl. It will be particularly preferred if $R^1$ is methyl and $R^2$ and $R^3$ are H or if $R^1$, $R^2$ and $R^3$ are methyl. The "X" in formula I of the mixture in the inventive process is selected from Cl, $SO_4$, $PO_4$, $CH_3COO$, $(COO)_2$, preferred is Cl.

The "n" in the formula I of the mixture of the inventive process is dependent of the valence of X in water a natural number selected from the group of 1, 2 and 3, preferably it will be 1 if X is Cl. The amount of compound b) in the mixture is in the range of 1 to 60 wt.-%, preferred is an amount in the range of 10 to 40 wt.-%.

The mixture of the invention comprises some byproducts as component c). The word "byproduct" in this application refer to all compounds that are not water or any other added solvents or compound b). Theses byproducts are received from the oxidation process and the hydrolyzation as it is described in U.S. Pat. No. 5,731,462 A. Compound c) comprises varying shares of byproducts. The ones with the largest share are chosen from the group of nitroalkanes, oximes, nitrones, amides, amines, aldehydes, aldol condensation products and mixtures of these products.

For the inventive process the mixture is put into a purification apparatus in step I). A purification apparatus is a device that separates the mixture by evaporating part of it. During the evaporation the composition of the residue always differs. However, it will refer in this application to the evaporated part as the "overhead product" and to the non-evaporated part—whatever the composition of the non-evaporated part is—as the "residue". In the context of this application wt.-% always refers to the weight percentage of the relevant component as referred to the entire composition, which can be the mixture, the residue or the overhead product.

The purification apparatus in step I) separates water and byproducts as overhead product of the mixture and of the residue without reducing the water content in the residue below 40 wt.-% during the whole separation. Such purification apparatus is selected from the group of distillation apparatus, distillation apparatus for a continuous steam distillation and packed column or plate column for a continuous countercurrent flow stripping process. Additionally, the purification apparatus has at least one access that allows to take samples of the residue before, during and after step III). This can be realized via bypass at the bottom of the purification apparatus. The preferred purification apparatus has also the possibility to take samples of the overhead product via bypass during and after step III) of the inventive process. The distillation apparatus and steam distillation apparatus are preferred for the inventive process.

In step II) of the inventive process the mixture gets in contact with steam in the purification apparatus. The mixture gets in contact with the steam so that a composition comprising water vapor and parts of the byproducts is received. This composition will be distillated in a separate flask during step III).

There are different ways how the steam gets in contact with the mixture in step II) of the inventive process. Either the steam will be fed in the purification apparatus by using a tube where the hot steam passes continuously through the mixture or even by heating the mixture or generating a vacuum in the purification apparatus so that the composition comprising water vapor and parts of byproducts will be formed wherein the heating is stopped or the vacuum is removed if the water content will be 40 wt.-% in the residue. The distillation that is started by heating or generating a vacuum can be stopped at any time before the water content in the residue is <40 wt. % in order to add additional amount of water to the residue and to start the distillation again by heating or generating a vacuum. Furthermore, the mixture can be passed through a packed or a plate column as it is used for a continuous countercurrent flow stripping process wherein the steam gets in contact with the mixture by passing the column in the opposite flow direction of the mixture as a countercurrent flow. Even here the composition comprising water vapor and byproducts will be distillated in a separated flask in step III). If the packed or a plate column is used it will be preferred that the column will be a vertical one and the mixture will pass the column from the top to the bottom while the steam will pass the column from the bottom to the top.

This is the normal process of stripping which is conducted in trayed towers (plate columns) and packed columns. Regarding the tray towers there are trays or plates inside the column. These trays force the liquid to flow back and forth horizontally while the vapor bubbles up through holes in the trays. The purpose of these trays is to increase the amount of contact area between the liquid and the vapor phases. In packed column which are similar to tray towers this problem is solved by using packings. All packings which are able to separate compound c) from the mixture or the residue are applicable in the inventive process.

The preferred way to bring the mixture in contact with steam in step II) of the invention will be if the steam is either continuously passed through the mixture via steam distillation or the steam is obtained by heating via distillation.

In step III) of the inventive process the composition comprising water vapor and byproducts will be removed from the mixture or the residue until the purity of compound b) in the residue is 95% or higher. This will be done by continuous condensation of the composition in a separated flask. The content of byproducts and compound b) in the residue will be controlled by taking 1H-NMR-spectrums of samples of the residue at different times during the separation of the overhead product. Purity of compound b) is herein defined as 100× the integral of the 1H-NMR peaks of compound b) divided by the sum of all integrals of all peaks of the spectrum wherein the integral of the water peak and the internal standard peak, if it is used, are excluded. The content of water in the residue is controlled by a Karl-Fischer titration.

The content of water in the residue is ≥40 wt.-%, preferred is the water content in the range of 40 to 80 wt.-%, particular preferred it is in the range from 50 to 80 wt.-%, more particular preferred it is in the range from 50 to 75 wt.-%. In order to keep the water content in the residue≥40 wt.-%, water can be added to the mixture before step II) or to the residue during or after the step III) of the inventive process. The water can be added as steam or liquid to the mixture or to the residue. Steam or water as liquid are added preferably during step III). After step III) water as liquid can also be added to the mixture wherein the amount of water rises over 40 wt.-% of the residue.

Advantageously, the amount of water that is added to the mixture or the residue of the inventive process before or during the distillation will be the same amount of water that is distilled off.

In the step III) of the inventive process the composition is removed by distillation. During distillation the temperature of the residue is in the range of 10 to 100° C., preferably in the range of 40 to 95° C. During distillation in step III) of the inventive process the pressure is in the range of 1 to 1000 mbar, preferably in the range from 10 to 750 mbar.

With the inventive process it is possible to receive a mixture which is easy and safety in handling and avoids the problems with the isolation of the pure N-alkyl-hydroxylammonium salt.

EXAMPLE 1

99 g (1.35 mol) of diethyl amine are dissolved in 95 ml water. While stirring this mixture 14.3 g of gaseous $CO_2$ are bubbled in over a period of 30 min. During the addition of $CO_2$ the temperature is kept below 40° C. via external cooling. 301 g of a 40 wt.-% $H_2O_2$ solution (3.54 mol $H_2O_2$) are then slowly added over a period of 6 hours. During the addition of $H_2O_2$ the temperature must be kept below 60° C. via external cooling and optionally by lowering the rate of $H_2O_2$ addition. The pH value of the solution is continuously controlled during the addition using a calibrated glass electrode. When the pH value drops below 10 aqueous NaOH solution (50 wt.-%) is added as required in order to keep the pH value slightly above 10. After addition of all reactants the mixture is stirred at 50° C. and samples are taken for peroxide titration (pH value still has to be kept above 10 by addition of NaOH). As soon as the peroxide value drops below 0.5 wt.-% $H_2O_2$ the reaction is completed, and temperature reduced to 20° C.

To this mixture 171.7 g HCl solution (37 wt.-% in water) are carefully added (dissolved $CO_2$ gases out during this procedure). The temperature is increased to 50° C. and the pressure reduced to allow a slight refluxing of the solution (~50-150 mbar). The condenser temperature has to be kept above 10° C. to allow for the removal of the acetaldehyde formed. After 4 hours of refluxing another portion of HCl solution (17 g) is added and refluxing continued for another 1.5 hours.

The solution still contains some intermediate and byproducts and has a purity of about 70% (NMR analysis: 400 MHz in $D_2O$: The mixture contains residual nitrone (typical peak: δ=3.92 ppm, 1H) N-ethyl-hydroxylammonium chloride (typical peak: δ=3.17 ppm, 2H), acetaldehyde oxime (typical peaks: δ=7.44 ppm, 7.19 ppm, 2 isomers, 1H each) and acetaldehyde (typical peak: δ=8.31 ppm, 1H), other peaks contribute less than 3% of the total integral, excluding water). For purification, the solution is transferred to a distillation apparatus. The temperature is increased to 50° C. and the pressure adjusted to allow a distillation of water (p<50 mbar). After about 50% of the water initially present in the mixture is distilled off, at which point the concentration of the hydroxylammonium salt is approximately 30-35 wt.-%, the same amount of water is added to the residue before distillation is continued. This procedure is repeated for a total of three times. In the last distillation step, the amount of water removed is adjusted in such a way that solution of the hydroxylammonium salt remaining in the sump has a concentration of approximately 30-35 wt.-%. The purity of this solution of N-ethyl-hydroxylammonium chloride is ~95% (via NMR analysis).

DSC analysis ($T_{initial}$=30° C.–$T_{final}$=410° C., $T_{ramp}$=2.5° C./min, glass crucible) of the purified aqueous solutions of N-ethyl-hydroxylammonium chloride and of the pure salt showed the following energy releases and onset temperatures (concentration determined by elemental analysis of the corresponding solutions) in Table 1:

TABLE 1

| Concentration (wt.-%) | Energy released (J/g) | Onset (° C.) |
|---|---|---|
| 27.8 | 583 | 75 |
| 43.3 | 872 | 67 |
| 61.1 | 1242 | 71 |
| 100 | 1989 | 78 |

EXAMPLE 2

91.5 g (0.91 mol) of diisopropyl amine are dissolved in 88.7 ml water and the mixture is homogenized by addition of 4.9 g methanol. To this mixture $CO_2$ is added and subsequently hydrogen peroxide solution is added as described in example 1. After acidification with HCl solution and refluxing for 4 h the solution still contains some intermediate and byproducts and has a purity of about 90% ((NMR analysis: 400 MHz in $D_2O$: The mixture contains N-isopropyl-hydroxylammonium chloride (typical peak: δ=3.60 ppm, 1H) and acetone (typical peak: δ=2.29 ppm, 6H); apart from the solvent peaks (methanol and water) other peaks contribute less than 3% of the total integral). For purification, the solution is transferred to a distillation apparatus. The temperature is increased to 50° C. and the pressure adjusted to allow a distillation of water (p<50 mbar). After about 50% of the solvent contained in the initial mixture is distilled off, at which point the concentration of the hydroxylammonium salt is approximately 30-35 wt. %, the same amount of water is added to the residue. This procedure is repeated in total three times. In the last distillation step, the amount of water removed is adjusted in such a way that solution of the hydroxylammonium salt remaining in the sump has a concentration of approximately 30-35 wt.-%. The purity of this solution of N-isopropyl-hydroxylammonium chloride is ~98% (via NMR analysis).

EXAMPLE 3

89.1 g (0.88 mol) N-tert-butyl-N-ethyl amine are dissolved in 91 ml of water. The mixture is treated with $CO_2$ and homogenized afterwards by the addition of 35 mL MeOH. Then, hydrogen peroxide is added as is described in example 1. After acidification with HCl solution and refluxing for 4 h the solution still contains some intermediate and byproducts and has a purity of about 90% based (NMR analysis: 400 MHz in $D_2O$: The mixture contains the desired product (δ=0.95 ppm, 9H), unconverted nitrone (typical peak: δ=7.33 ppm, 1H) and acetaldehyde (typical peak: δ=8.30 ppm, 1H); apart from solvents (methanol and water) other peaks contribute less than 3% of the total integral). For purification and liberation of N-tert-butyl hydroxylamine, the solution is transferred to a distillation apparatus. The temperature is increased to 50° C. and the pressure adjusted to allow a distillation of water (p<50 mbar). After about 50% of the solvent contained in the initial mixture are distilled off, at which point the concentration of the hydroxylammonium salt is approximately 35-40 wt.-%, the same amount of water is added to the residue. This procedure is repeated in total three times. In the last distillation step, the amount of water removed is adjusted in such a way that solution of the hydroxylammonium salt remaining in the sump has a concentration of approximately 35-40 wt.-%. The purity of this solution of N-tert-butyl-hydroxylammonium chloride is ~99% (via NMR analysis).

The invention claimed is:

1. Process for the purification of a mixture comprising three compounds:
   a) water,
   b) 1 to 60 wt.-% of N-alkyl hydroxylammonium salt of formula I and

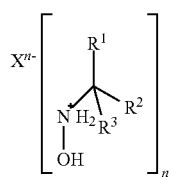

I wherein:
   R1, R2, R3 each independently are selected from the group of H, methyl, ethyl, n-propyl, isopropyl, n-butyl, 2-butyl and tert-butyl,
   X is selected from Cl, $SO_4$, $PO_4$, $CH_3COO$, $(COO)_2$,
   n dependent of the valence of X in water is a natural number selected from the group of 1, 2 and 3 and
   c) byproducts
   wherein the process comprises the following steps:
   I) putting the mixture into a purification apparatus,
   II) bringing the mixture in contact with steam
   III) removing a composition comprising water vapor and the byproducts in c) by distillation until the purity of the compound of formula I in b), in the residue is 95% or greater wherein the amount of water in the residue remains during and after the distillation≥40 wt. %.

2. The process according to claim 1, wherein the purification apparatus is a packed column as it is used for a continuous reverse flow stripping process.

3. The process according to claim 1, wherein the purification apparatus is a distillation apparatus.

4. The process according to claim 3, wherein the purification apparatus is a steam distillation apparatus.

5. The process according to claim 1, wherein water is added either before step II) and/or during and/or after distillation of step III).

6. The process according to a claim 5, wherein the water that is added during the distillation of step III) in a steam distillation apparatus or in the packed column as it is used for continuous reverse flow stripping process is added as steam.

7. The process according to claim 5, wherein the water that is added during the distillation of step III) in a distillation apparatus is added according to the following steps:
   i) stopping the distillation,
   ii) adding the water in liquid form to the residue and
   iii) starting the distillation again.

8. The process according to claim 1, wherein the distillation temperature during step III) is in the range of 10 to 100° C. and the pressure is in the range of 1 to 1000 mbar.

9. The process according to claim 1, wherein the composition distilled off in step III) comprises more than 50 wt. % of water.

10. The process according to claim 1, wherein X is Cl and n is 1.

11. The process according to a claim 1, wherein $R^1$ is ≠$R^2$ and $R^3$ is H.

12. The process according to claim 1, wherein $R^1$ is methyl, $R^2$ and $R^3$ are H, X is Cl and n is 1.

13. The process according to claim 1, wherein none of $R^1$, $R^2$ and $R^3$ is H.

* * * * *